(12) United States Patent
Sumida et al.

(10) Patent No.: US 6,506,932 B2
(45) Date of Patent: Jan. 14, 2003

(54) METHOD FOR PRODUCTION OF OXYGEN-CONTAINING AROMATIC COMPOUND

(75) Inventors: Yasutaka Sumida, Neyagawa (JP); Masahiro Wada, Nishinomiya (JP); Noritaka Mizuno, Tokyo (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 10/039,757

(22) Filed: Nov. 7, 2001

(65) Prior Publication Data

US 2002/0133043 A1 Sep. 19, 2002

(30) Foreign Application Priority Data

Nov. 10, 2000 (JP) .......................... 2000-343673
Nov. 10, 2000 (JP) .......................... 2000-343685
Nov. 10, 2000 (JP) .......................... 2000-343743

(51) Int. Cl.$^7$ .................. C07C 51/16; C07C 51/255; C07C 45/90
(52) U.S. Cl. .................. 562/412; 568/426; 568/431
(58) Field of Search .................. 562/412; 568/426, 568/431

(56) References Cited

U.S. PATENT DOCUMENTS 5,760,288 A   6/1998   Asahi et al. ................. 562/412

FOREIGN PATENT DOCUMENTS

| EP | 1 112 777 A1 | 7/2001 | .......... B01J/27/188 |
| JP | 08-053391 | 2/1996 | .......... C07C/63/00 |
| JP | 09-169694 | 6/1997 | .......... C07C/63/26 |
| JP | 09-286756 | 11/1997 | .......... C07C/63/00 |
| JP | 09-286757 | 11/1997 | .......... C07C/63/26 |
| JP | 11-001447 | 1/1999 | .......... C07C/27/00 |
| JP | 2000-103758 | 4/2000 | .......... C07C/45/36 |

OTHER PUBLICATIONS

Database WPI Section Ch, Week 199618 Derwent Publications Ltd., London, GB; Class A41, AN 1996–175688, XP002189451 and JP 08 053391 A (Mitsubishi Chem Corp), Feb. 27, 1996.

Mitzuno et al., "Highly Efficient Uitlization of Hydrogen Peroxide for Selective Oxygenation of Alkanes Catalyzed by Diiron–Substituted Polyoxometalate Precursor", J. Am. Chem. Soc 120:9267–9272, 1998.

Primary Examiner—Mukund J. Shah
Assistant Examiner—Zachary Tucker
(74) Attorney, Agent, or Firm—Fish & Richardson P.C.

(57) ABSTRACT

A method for oxidizing an aromatic compound possesssing at least one alkyl substituent by using a catalyst avoids containing a corrosive bromine ion, remains stably without being decomposed even in an oxidizing atmospherfe, and permits reclamation is provided. An aromatic compound possessing at least one alkyl substituent is oxidized by using a catalyst which has at least one kind of element selected from the group consisting of phosphorus, silicon, and germanium as a hetero atom and at least one kind of element selected from the group consisting of molybdenum, tungsten, vanadium, and niobium as a poly atom and comprises a heteropoly-oxometalate anion possessing two defective structure site and at least one kind of element selected from the group of elements of Periods 4~6 of Groups IB, VA, VIIA, and VIII in the Periodic Table of the Elements.

12 Claims, 1 Drawing Sheet

US 6,506,932 B2

METHOD FOR PRODUCTION OF OXYGEN-CONTAINING AROMATIC COMPOUND

BACKGROUND OF THE INVENTION

1. Field of the Invention

This invention relates to a method for producing an oxygen-containing aromatic compound by oxidizing an alkyl group of an aromatic compound possessing at least one alkyl substituent group.

2. Description of the Related Art

Heretofore, a method for producing an aromatic carboxylic acid, for example, by oxidizing an alkyl group of an aromatic compound possessing at least one alkyl substituent has been carried out in a liquid phase using a lower alkanoic acid typified by acetic acid or water as a solvent in the presence of a bromine compound or a compound of such a transition metal as cobalt or manganese.

JP-A-2000-103,758 discloses a method for producing an aromatic ketone by subjecting an aromatic compound possessing R—$CH_2$— group to liquid-phase oxidation. The heteropoly acid which is used in this production is such a heteropoly acid as lacks a defective structure site and the production is aimed at an aromatic ketone. JP-A-08-53,391, JP-A-09-169,694, and JP-A-09-286,756 disclose methods for producing an aromatic carboxylic acid in an aqueous medium using as a catalyst a compound having a transition metal incorporated in a heteropoly acid skeleton possessing a defective structure site. JP-A-09-286,757 discloses a method for producing an aromatic carboxylic acid by using a catalyst obtained by thermally treating a heteropoly acid ion possessing a defective structure site and a transition metal salt in an aqueous medium at a temperature of not lower than 100° C. JP-A-11-1,447 discloses a method for producing an aromatic carboxylic acid in an aqueous solution in the presence of a heteropoly acid or a salt thereof or a transition metal not incorporated in a heteropoly acid. Though these disclosures indicate use of heteropoly acid catalysts in the production of aromatic carboxylic acids, they have no specific mention of a heteropoly acid catalyst which possesses two defective structures.

This invention has for an object thereof the provision of a method for producing an oxygen-containing aromatic compound by oxidizing an aromatic compound possessing at least one alkyl substituent while avoiding use of a corrosive bromine ion as a catalyst and nevertheless using a catalyst so stable as to shun decomposition and also reusable even in an oxidizing atmosphere.

SUMMARY OF THE INVENTION

The object mentioned above is accomplished by a method for the production of an oxygen-containing aromatic hydrocarbon by the oxidation of an alkyl group of an aromatic compound possessing at least one alkyl substituent with a molecular oxygen-containing gas, which comprises effecting the oxidation by the use of a catalyst having a hetero atom formed of at least one element selected from among phosphorus, silicon, and germanium and a poly atom formed of at least one element selected from among molybdenum, tungsten, vanadium, and niobium and comprising a heteropolyoxometalate anion possessing two defective structure sites and at least one element selected from the group consisting of the elements of Periods 4~6 of Groups IB, VA, VIIA, and VIII in the Periodic Table of the Elements.

The method of this invention is enabled, by oxidizing an aromatic compound possessing at least one alkyl group in the presence of a catalyst not entailing corrosion of apparatus and operating effectively in the least possible application rate, to produce a useful oxygen-containing aromatic carbonyl compound and/or aromatic carboxylic acid.

PREFERRED EMBODIMENT OF THE INVENTION

Figure 1:
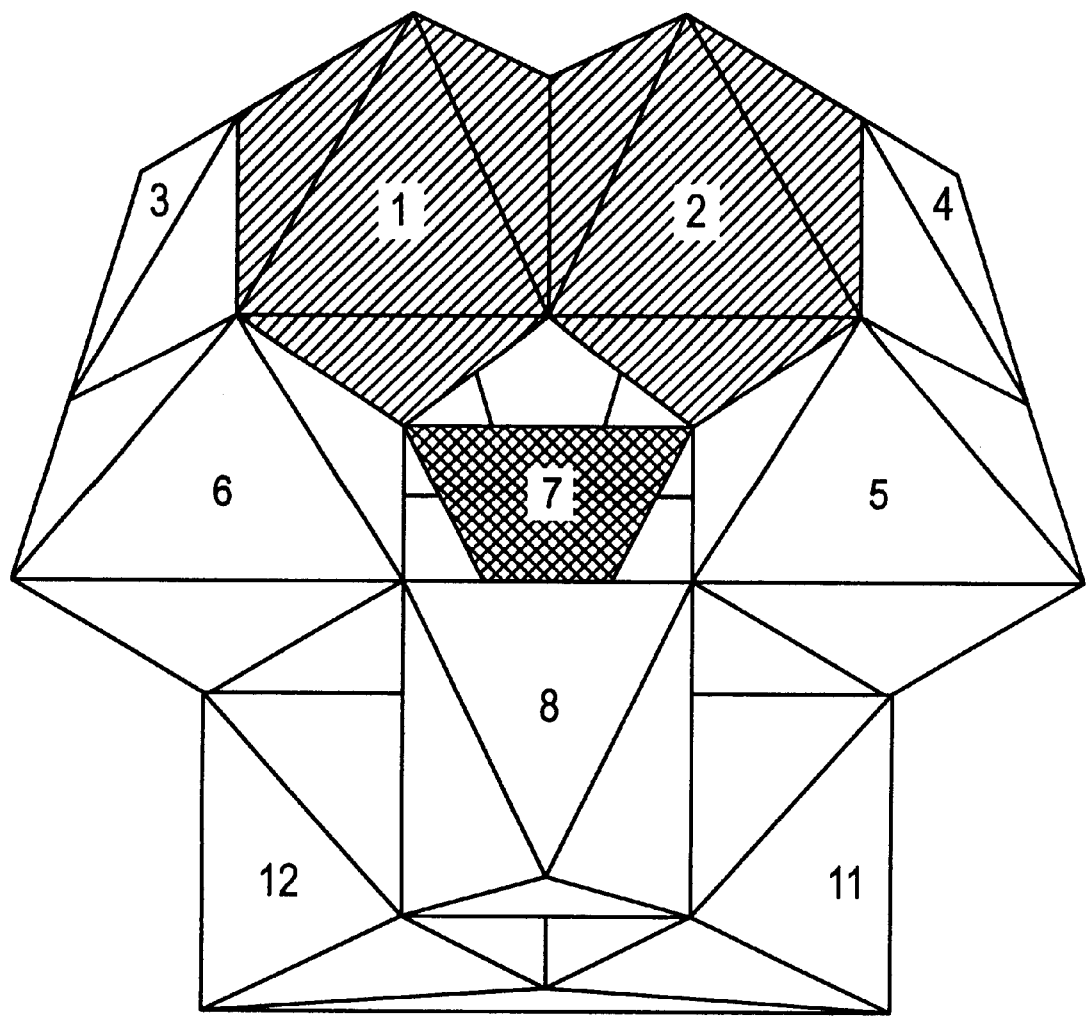
FIG. 1 illustrates the molecular structure of a polyoxometalate $[\gamma\text{-SiW}_{10}\{M\}_2O_{38}]^{q-}$ substituted by two typical metal ions. M is indicated by a shaded (with a hatched area) octahedron. $WO_6$ is indicated by a white octahedron. $SiO_2$ is indicated by a black-centered (in the manner of space lattice) tetrahedron. The numerals shown in the diagram each represent a variable n in $W_n$, which represents $WO_6$ in the Keggin structure and denotes the number based on IUPAC.

Now, this invention will be described in detail below. The catalyst to be used in this invention is a catalyst which has a hetero atom formed of at least one element selected from among phosphorus, silicon, and germanium and a poly atom formed of at least one element selected from among molybdenum, tungsten, vanadium, and niobium and comprises a heteropolyoxometalate anion possessing two defective structure sites and at least one element selected from the group consisting of the elements of Periods 4~6 of Groups IB, VA, VIIA, and VIII in the Periodic Table of the Elements. The at least one element to be selected from the group consisting of elements of Periods 4~6 of Groups IB, VA, VIIA, and VIII in the Periodic Table of the Elements is preferably V, Mn, Fe, Co, Ni, or Au and particularly preferably V or Au. The at least one element to be selected from the group consisting of elements of Periods 4~6 of Groups IB, VA, VIIA, and VIII in the Periodic Table of the Elements may be at least partly incorporated or may not be incorporated in the heteropolyoxometalate anion skeleton possessing two defective structure sites in the catalyst.

Further, in this invention, when the at least one element selected from the group consisting of elements of Periods 4~6 of Groups IB, VA, VIIA, and VIII in the Periodic Table of the Elements is incorporated in the heteropolyoxometalate anion skeleton possessing two defective structure sites, this element is preferred to be incorporated therein at a ratio of two pieces per piece of the heteropolyoxometalate anion possessing two defective structure sites and more preferred to be incorporated therein in such a pattern that the two pieces mutually form an edge sharing. The at least one element selected from the group consisting of elements of Periods 4~6 of Groups IB, VA, VIIA, and VIII in the Periodic Table of the Elements is preferred to be present in an amount of not less than 0.001 atoms per molecule of the heteropolyoxometalate anion.

The skeleton of heteropolyoxometalate anion possessing two defective structure sites which is used herein possesses a Keggin type heteropoly acid ion structure. This structure is represented by the following general formula (1)

$$[Y_1M_{10}O_{36}]^{q-} \tag{1}$$

wherein Y is at least one kind of element selected from the group consisting of silicon, germanium, and phosphorus, M is at least one kind of element selected from the group consisting of molybdenum, tungsten, vanadium, and niobium, and q is an integer decided by the numerals of valency of the elements Y and M.

This structural formula is so illustrated in FIG. 1 as to facilitate its comprehension. The preparation of the heteropolyoxometalate anion possessing two defective structure sites which is used in this invention, for example, can be executed by a method which is reported by Mizuno, et al. In J. Am. Chem. Soc. 1998, 120, 9267. Generally, the Keggin type heteropolyoxometalate anion possessing two defective structure sites has isomers of the γ type, δ type, and ε type. This invention prefers this anion to be in the γ type. As the counter ion to the heteropolyoxometalate anion possessing two defective structure sites, proton and such alkali metal ions as Na, K, and Rb which are soluble in water are advantageously used where the reaction of oxidation is carried out in an aqueous medium and tetraalkyl ammonium ion and pyridium ion substituted with an alkyl group are used where the reaction is carried out in an organic solvent. No restriction is imposed on the selection of the counter ion.

The incorporation of the at least one element selected from the group consisting of elements of Periods 4~6 of Groups IB, VA, VIIA, and VIII in the Periodic Table of the Elements in the heteropolyoxometalate anion skeleton possessing two defective structure sites can be optionally attained by dissolving the heteropolyoxometalate anion in a solvent, adding a compound of the at least one element selected from the group consisting of elements of Periods 4~6 of Groups IB, VA, VIIA, and VIII in the Periodic Table of the Elements to the resultant solution, and subjecting the produced reaction mixture to a heat treatment. The amount of the catalyst to be used in this invention, as expressed in the molar ratio of the catalyst to the reaction substrate, is in the range of 1:1~1:1,000,000, preferably in the range of 1:10~1:100,000.

As the reaction substrate for use in this invention, an aromatic compound possessing at least one alkyl substituent is used. The alkyl group is generally in such a size as has the number of carbon atoms in the approximate range of 1~8. As typical examples of the preferred alkyl group, methyl group, ethyl group, propyl group, and isopropyl group may be cited. As typical examples of the aromatic ring, such polycyclic aromatic rings as naphthalene ring may be cited.

As typical examples of the aromatic compound, aromatic compounds containing hetero elements including the elements of nitrogen and sulfur such as pyridine compounds and thiophene compounds may be also cited. This invention is applied to such aromatic compounds as are further substituted with a hydroxyl group, a carbonyl group, and a carboxyl group other than the alkyl groups.

These starting raw materials are usable without being discriminated on account of the kind of method adopted for the production. As typical examples of these compounds, toluene, ethyl benzene, ethyl toluene, diethyl benzene, isopropylethyl benzene, isopropyl benzene, n-propyl benzene, 4,4'-dimethyl biphenyl, cumene, butyl benzene, 4-t-butyl-1-methyl benzene, 3-ethyl toluene, 4-ethyl toluene, chloroethyl benzene, dichloroethyl benzene, nitroethyl benzene, o-, m-, p-cresol, o-, m-, p-xylene, o-, m-, p-diisopropyl benzene, 1,2,3-trimethyl benzene, 1,2,4-trimethyl benzene, 1,3,5-trimethyl benzene, 1,2,4,5-tetramethyl benzene, o-, m-, p-toluic acid, o-, m-, p-tolualdehyde, 2,4-dimethyl benzaldehyde, 2,4,5-trimethyl benzaldehyde, and mixtures thereof may be cited.

The aromatic carbonyl compound, i.e. a compound obtained by this invention, is an aromatic compound which possesses a carbonyl group directly in the aromatic ring thereof. As typical examples of the aromatic carbonyl compound, benzaldehyde, acetophenone, hydroxy benzaldehyde, carboxy benzaldehyde, and acetoxy benzaldehyde may be cited. The aromatic carboxylic acid, i.e. a compound obtained by this invention, is an aromatic compound containing at least one carboxyl group directly in the aromatic ring thereof. As typical examples of the aromatic carboxylic acid, benzoic acid, telephthalic acid, and hydroxybenzoic acid may be cited.

Incidentally, the transformation of the alkyl group attached to the aromatic ring eventually to the carboxyl group by dint of oxidation is presumed to proceed via a corresponding carbonyl group. The oxidation of toluene, for example, is thought to proceed via benzaldehyde and, with further progress thereof, eventually reach benzoic acid.

The oxidation contemplated by this invention is effected by a method of causing a reaction substrate to contact a molecular oxygen-containing gas in the presence of a catalyst. The reaction can be carried out in a homogeneous liquid phase system obtained by dissolving the catalyst and the reactants in a typical solvent. As the typical solvent, water or an organic solvent which is generally inert to the reaction is used. It is naturally permissible to perform the reaction in either a mixed system or a two-phase system to be formed between water and the organic solvent. As typical examples of the typical solvent, alkanoic acids such as acetic acid and propionic acid, nitrites such as acetonitrile, propionitrile, and benzonitrile, amides such as formamide, acetamide, and dimethyl formamide; aromatic hydrocarbons such as benzene and naphthalene, aliphatic hydrocarbons such as hexane and octane, halogenated hydrocarbons such as chloroform, dichloromethane, dichloroethane, and chlorobenzene, nitro compounds such as nitrobenzene and nitromethane, esters such as ethyl acetate and butyl acetate, ethers such as dimethyl ether and tetrahydrofuran, dimethyl sulfoxide, and mixtures there of maybe cited. Some substrates may serve as solvents. When the solvent excluding such a reaction substrate is adopted, the weight ratio of the solvent to the reaction substrate is selected in the range of 1:10~1000:1, preferably in the range of 1:1~100:1. The solvent may be suspended in a liquid phase instead of being dissolved in a solvent. The so-called heterogeneous reaction system which has the catalyst as a solid phase and the reactants as a gas phase is also usable. The catalyst may be deposited on a carrier or may be directly used as a solid of itself and the reaction substrate may be added thereto. As the carrier for the catalyst, such carriers as various kinds of ion-exchange resins, silica, alumina, and oxides which are generally used for the heterogeneous catalytic reaction are usable.

The molecular oxygen-containing gas to be used in this invention may be pure oxygen or the oxygen which is diluted with such an inert gas as nitrogen, helium, argon, or carbon dioxide. Air proves advantageous in terms of safety, practicability, and economy. The amount of the molecular oxygen-containing gas to be used can be selected to suit the kind of the reaction substrate and the kind of the target compound to be produced. It is properly not less than 0.01 mol, preferably in the range of 0.1~100 mols, and more preferably in the range of 1~50 mols, as reduced to molecular oxygen per mol of the substrate.

The reaction temperature is generally in the range of 0°~350° C., preferably in the range of 50°~250° C., and more preferably in the range of 100°~220° C.

The reaction may be performed under either normal pressure or high pressure. It is generally in the range of normal pressure ~10 MPa and preferably in the range of normal pressure ~8 Mpa.

The reaction time is selected to suit the reaction temperature, the reaction pressure, and the kind of the catalyst to be used. It is selected, for example, in the range of 10 minutes~100 hours and preferably in the range of 2~48 hours.

The pH of the reaction solution, in consideration of the stability of the catalyst, is adjusted from time to time as with a pH buffer.

The oxygen-containing aromatic compound produced in consequence of the execution of this invention is separated and refined by a various method, such as, for example, filtration, centrifugation, or distillation. The solution remaining after the separation of the target oxygen-containing aromatic compound and containing the used catalyst may be reclaimed, sometimes after having the solution replenished with fresh supply of catalyst.

Now, this invention will be described more specifically below with reference to working examples thereof, which are not limitative of this invention. The following working examples illustrate modes of embodying this invention.

Preparation of Potassium Salt of Two Defective Structure Type γ-tungstosilicic Acid ($K_8$[γ-$Si_1W_{10}O_{36}$].12$H_2O$)

(Preparation of one Defective Structure Type ($K_8$[$β_2$-$Si_1W_{11}O_{39}$].14$H_2O$)

A beaker was charged with 182 g of sodium tungstate dihydrate and 300 ml of water. To the produced liquid, 165 ml of a 4 mol/liter hydrochloric acid solution was added as kept stirred over a period of about 10 minutes. The resultant reaction solution and an aqueous solution prepared separately with 14.2 g of sodium silicate nonahydrate in 100 ml were together kept at a pH in the range of 5~6 with a 4 mol/liter hydrochloric acid solution and stirred at room temperature for 15 minutes until completion of the reaction. The resultant solution was subjected to salting out by the addition of 90 g of potassium chloride. The white solid consequently formed was recovered by filtration and the filtrate was purified by washing with 100 ml of an aqueous 2 mol/liter KCl solution. The solid consequently recovered was air-dried for 12 hours to obtain ($K_8$[$β_2$-$Si_1W_{11}O_{39}$].14$H_2O$).

(Preparation of Two Defective Structure Type $K_8$[γ-$Si_1W_{10}O_{36}$].12$H_2O$)

The amount 30 g of the one defective structure type ($K_8$[$β_2$-$Si_1W_{11}O_{39}$].14$H_2O$) obtained as described above was dissolved in 100 ml of water. When this solution formed any insoluble component, it was immediately deprived of the insoluble component by filtration. The solution was promptly adjusted to pH 9.1 by addition of a 2 mol/liter $K_2CO_3$ solution. It was kept stirred continuously for 16 minutes as kept at the pH value mentioned above. Subsequently, it was subjected to salting out by the addition of 80 g of potassium chloride. The produced solution was filtered, the filtrate was washed further with 100 ml of a 1 mol/liter KCl solution, and the washed solution was air-dried for 12 hours to obtain the two defective structure type $K_8$[γ-$Si_1W_{10}O_{36}$].12$H_2O$.

Catalyst A (Preparation of a Salt of Two Substitution Type Tungstosilicic Acid Substituted With the Element of Iron [$(C_4H_9)_4N$]$_{3.6}H_{2.5}$[γ-$Si_1W_{10}${Fe$(OH_2)_2$}$_2O_{38}$].$H_2O$)

The amount 3.0 g of the two defective type $K_8$[γ-$Si_1W_{10}O_{36}$].12$H_2O$ was dissolved in 30 ml of water, adjusted to pH 3.9 with concentrated nitric acid, and stirred together with an aqueous solution of 0.81 g of ferric nitrate nonahydrate in 5 ml of water for five minutes. Then, the formed solution was stirred together with 3.04 g of tetrabutyl ammonium nitrate added thereto for 15 minutes. The whitisi yellow solid consequently formed was subjected to filtration under reduced pressure and dried. The solid consequently recovered was dissolved in 15 ml of acetonitrile, stirred together with 300 ml of water added slowly thereto and meanwhile immersed in ice water to induce recrystallization. The yellowish brown solid consequently formed was recovered by filtration, washed twice with 50 ml of water, and then dried under reduced pressure. This procedure of recrystallization was repeated once more to obtain the catalyst A. (Hereinafter, this catalyst will be referred to as "Fe-POM")

Catalyst B (Preparation of γ-Keggin Type Two Defective Structure Heteropolyoxometalate Compound Substituted with the Element of Mn)

The amount 3.0 g of the two defective structure type $K_8$[γ-$Si_1W_{10}O_{36}$].12$H_2O$ was dissolved and acidified in 30 ml of deionized water, then stirred together with 0.57 g of manganese nitrate (II) hexahydrate added thereto, and combined with 4.1 g of tetrabutyl ammonium nitrate to produce a precipitate. The precipitate was separated by filtration, dissolved in 15 ml of acetonitrile, then reprecipitated by the addition of 300 ml of water. The resultant product was purified by performing the procedure described above up to two repetitions to obtain the catalyst B. (Hereinafter, this catalyst will be indicated as "Mn-POM.")

Catalyst C (Preparation of γ-Keggin Type Two Defective Structure Heteropolyoxometalate Compound Substituted with the Element of Co)

This catalyst was prepared by following the procedure adopted for the preparation of Catalyst A while using the ferric nitrate nonahydrate to 0.58 g of cobalt nitrate (II) hexahydrate in the place of the ferric nitrate nonahydrate used in the preparation of Catalyst A (hereinafter the catalyst will be indicated as "Co-POM".)

Catalyst D (Preparation of Potassium Salt Compound of γ-Keggin Type Two Defective Structure Heteropolyoxometalate Substituted with the Element of Co)

The amount 3.0 g of the two defective structure type $K_8$[γ-$Si_1W_{10}O_{36}$].12$H_2O$ was dissolved in 30 ml of water, adjusted to pH 3.9 with concentrated nitric acid, and stirred for 5 minutes together with an aqueous solution of 0.58 g of cobalt nitrate (II) hexahydrate in 5 ml of water. Then, the resultant solution was concentrated till dryness under reduced pressure. The solid consequently obtained was dissolved in 100 ml of water, caused to form a precipitate with added ether, filtered to separate the precipitate, and deprived the solid precipitate of the ether under reduced pressure to obtain a potassium salt compound of the γ-Keggin type two defective structure type heteropolyoxometalate substituted with the element of Co (hereinafter, the catalyst will be indicated as "Co-POM-K").

Catalyst E (Preparation of γ-Keggin Type Two Defective Heteropolyoxometalate Compound Substituted with the Element of Ni)

This catalyst was prepared by following the procedure adopted for the production of Catalyst A while using 0.58 g of nickel nitrate (II) hexahydrate in the place of the ferric nitrate nonahydrate used in the preparation of Catalyst A (hereinafter the catalyst will be indicated as "Ni-POM").

Catalyst F (Preparation of γ-Keggin Type Two Defective Heteropolyoxometalate Compound Substituted with the Element of V)

The amount 3.0 g of the two defective structure type $K_8[\gamma\text{-}Si_1W_{10}O_{36}]\cdot 12H_2O$ was dissolved in 11 ml of a 1 mol/liter HCl solution, adjusted to pH 3.9 with concentrated nitric acid, and then stirred for 5 minutes together with 4.1 ml of a 0.5 mol/liter $NaVO_3$ aqueous solution. The solution consequently obtained was filtered to remove a precipitate formed therein and then stirred for 15 minutes together with 2.654 g of tetrabutyl ammonium bromide added thereto. The whitish yellow solid consequently formed was dried under reduced pressure. The recovered solid was dissolved in 15 ml of acetonitrile, stirred together with 300 ml of water slowly added thereto, and immersed meanwhile in ice water to undergo recrystallization. The yellowish brown solid consequently formed was recovered by filtration, washed twice with 50 ml of water, and then dried under reduced pressure. The procedure of this recrystallization was repeated once more to obtain Catalyst F (hereinafter this catalyst will be indicated as "V-POM").

Catalyst G (Preparation of γ-Keggin Type Two Defective Heteropolyoxometalate Compound Substituted with the Element of Au)

This catalyst was prepared by following the procedure adopted for the preparation of Catalyst A while using an aqueous solution having 0.82 g of chloroauric acid tetrahydrate dissolved in 5 ml of water in the place of ferric nitrate nonahydrate used in the preparation of Catalyst A (hereinafter this catalyst will be indicated as "Au-POM").

Catalyst H (Preparation of the One Substitution Type Tungstosilicate Substituted with the Element of Iron: $[(C_4H_9)_4N]_{4.25}H_{0.75}[\alpha\text{-}SiW_{11}\{Fe(OH_2)\}O_{39}])$ The amount 32 g of the one defective type $K_8[\beta_2\text{-}SiW_{11}O_{39}]\cdot 14H_2O$ was dissolved in 60 ml of water heated in advance to 95° C. The resultant solution was combined with 4.1 g of ferric nirate nonahydrate. After the elapse of 10 minutes, the produced solution was filtered. The filtrate was combined with 100 ml of a solution of methanol-ethanol mixture (1:1 (v/v)). The precipitate consequently formed was recovered by filtration and further refined with a solution of water-methanol mixture to obtain $K_5[SiW_{11}\{Fe(OH)_2\}O_{39}]\cdot 14H_2O$. The precipitate which was formed by adding 4.3 g of tetrabutyl ammonium bromide to the aqueous solution of 2.5 g of this potassium salt was dissolved with acetonitrile, caused to induce precipitation with water, and refined by repeating the procedure mentioned above to obtain an iron one substitution type tungstosilicate: $[(C_4H_9)_4N]_{4.25}H_{0.75}[\alpha\text{-}SiW_{11}\{Fe(OH_2)\}O_{39}])$ (hereinafter this catalyst will be indicated as "1-POM-Fe").

Catalyst I (Preparation of Three Substitution Type Tungstosilica Substituted with the Element of Iron: $[(C_4H_9)_4N]_{3.25}H_{3.75}[\alpha\text{-}SiW_9\{Fe(OH_2)\}_3O_{37}])$ Preparation of Three Defective Structure Type $Na_{10}[\alpha\text{-}SiW_9O_{34}]\cdot 18H_2O$ In 200 ml of hot water at 85° C., 182 g of sodium tungstate dihydrate and 11 g of sodium silicate nonahydrate were dissolved and stirred for 30 minutes. To the solution resulting from the agitation, 130 ml of a 6 mol/liter HCl aqueous solution was added dropwise. The produced solution was concentrated till an approximate volume of 300 ml and then filtered. The filtrate and an aqueous solution of 50 g of anhydrous sodium carbonate in 150 ml of water slowly added thereto were together stirred continuously for three hours. The white precipitate consequently formed was filtered. The filtrate was dispersed in 1000 ml of a 4 mol/liter NaCl aqueous solution and further stirred for one hour. Thereafter, the white precipitate was filtered, then washed twice with 100 ml of ethanol further washed with 100 ml of ethyl ether to obtain a three defective structure type $Na_{10}[\alpha\text{-}SiW_9O_{34}]\cdot 18H_2O$.

The amount 6.8 g of $CH_3COONa\cdot 3H_2O$ was dissolved in 100 ml of water and the produced solution was combined a solution obtained by dissolving 5.39 g of ferric nitrate nonahydrate in 15 ml of water. The solution consequently formed was heated to 70° C. To the heated solution, 11.25 g of the three defective structure type $Na_{10}[\alpha\text{-}SiW_9O_{34}]\cdot 18H_2O$ obtained by the procedure described above was added over a period of one hour. Subsequently, the resultant mixture was stirred for one hour and cooled to normal room temperature. The solution obtained consequently was passed three times through a bed of a $Na^+$ type cation-exchange resin. The yellowish brown clear solution consequently obtained and an aqueous solution of 16.8 g of tetrabutyl ammonium bromide in 40 ml of water added thereto were stirred at room temperature for one hour and then filtered. The yellowish brown solid recovered by the filtration was dissolved in 40 ml of acetonitrile, stirred in an ice water bath for one hour together with 500 ml of water added thereto, then filtered, and dried overnight at room temperature to obtain an iron three substituion type tungstosilicate $[(C_4H_9)_4N]_{3.25}H_{3.75}[\alpha\text{-}SiW_9\{Fe(OH)_2\}_3O_{37}]$(hereinafter the catalyst will be indicated as "3-POM-Fe").

Catalyst J <<Preparation of Potassium Salt of γ-Keggin Type Two Defective Heteropolyoxometalate Substituted with Two Atoms of Mn: $K_6[SiW_{10}\{Mn(OH_2)\}_2O_{36}]\cdot 23H_2O$>>

Ten g of $K_6[\gamma\text{-}SiW_{10}O_{36}]\cdot 12H_2O$ was dissolved in 40 ml of water. To the solution consequently formed, a solution obtained by dissolving 1.6 g of manganese acetate (II) dihydrate in 15 ml of water and adjusted to pH 3.9 with acetic acid was added dropwise. The resultant mixture was stirred for 5 minutes and then combined with 20 g of KCl. The precipitate was filtered. The filtrate was dissolved in 15 ml of water at 80° C., subjected to reprecipitation in an ice water bath, and filtered to obtain $K_6[SiW_{10}\{Mn(OH_2)\}_2O_{36}]\cdot 23H_2O$ (hereinafter indicated as "K-POM-Mn").

EXAMPLE 1

Toluene was oxidized. A reaction vessel containing 5 ml of dimethyl sulfoxide, 1.5 ml of 1,2-dichloroethane, and 0.1 ml of acetonitrile as solvents was charged with 1.5 μmols of Catalyst A and 19 m.mols of toluene and cooled to 0° C. The reaction vessel, after having the gas phase part thereof filled to capacity with pure oxygen, was stoppered, then immersed in an oil bath kept at 180° C., and vigorously shaken for 24 hours. Then, the reaction solution was cooled to room temperature and the product was analyzed by liquid chromatography. It was consequently found that the yield of benzaldehyde was 0.6 mol % and the yield of benzoic acid was 2.7 mol % based on the amount of toluene charged. After completion of the reaction, the reaction solution was dried under reduced pressure to remove the organic matter entrained thereby. The residue remaining after this removal was reclaimed as Catalyst A for use in Example 2. The results of this experiment are shown in Table 1.

EXAMPLE 2

The reaction was performed by following the procedure of Example 1 while using the residue remaining after the removal of the organic matter from the reaction solution of Example 1 by drying under reduced pressure in the place of Catalyst A and using 15 ml of acetic acid as a solvent. The results of this experiment are shown in Table 1. Thus, the catalyst was found to be reclaimed.

EXAMPLE 3

Toluene was oxidized by following the procedure of Example 1 while using Catalyst D instead and using 15 ml of water as a solvent. The results of this experiment are shown in Table 1.

EXAMPLE 4

Toluene was oxidized by following the procedure of Example 1 while using 1.5 $\mu$mol of two defective structure potassium salt $K_8[\gamma\text{-}SiW_{10}O_{38}]\cdot 12H_2O$ and 4 $\mu$mol of ferric nitrate nonahydrate as catalysts and using 15 ml of water alone as a solvent. The results of this experiment are shown in Table 1.

EXAMPLE 5

Toluene was oxidized by following the procedure of Example 1 while using Catalyst C instead as a catalyst. The results of this experiment are shown in Table 1.

EXAMPLE 6

Toluene was oxidized by following the procedure of Example 1 while using Catalyst E instead as a catalyst. The results of this experiment are shown in Table 1.
Control 1
Toluene was oxidized by following the procedure of Example 1 while using Catalyst H in the place of Catalyst A as a catalyst. The results of this experiment are shown in Table 1.
Control 2
Toluene was oxidized by following the procedure of Example 1 while using Catalyst I in the place of Catalyst A as a catalyst. The results of this experiment are shown in Table 1.

EXAMPLE 7 p-Cresol was oxidized by following the procedure of Example 1 while using p-cresol in the place of toluene as a reaction substrate and using Catalyst F instead as a catalyst. The results of this experiment are shown in Table 1.

EXAMPLE 8

Ethylbenzene was oxidized by following the procedure of Example 1 while using ethyl-benzene in the place of toluene as a reaction substrate and using Catalyst F instead as a catalyst. The results of this experiment are shown in Table 1.

EXAMPLE 9

Acetoxy toluene was oxidized by following the procedure of Example 1 while using acetoxy toluene in the place of toluene as a reaction substrate and using Catalyst F instead as a catalyst. The results of this experiment are shown in Table 1.

EXAMPLE 10 p-Toluylic acid was oxidized by following the procedure of Example 1 while using p-toluylic acid in the place of toluene as a reaction substrate, Catalyst F instead as a catalyst, and water as a solvent. The results of this experiment are shown in Table 1.

EXAMPLE 11 p-Xylene was oxidized by following the procedure of Example 1 while using p-xylene in the place of toluene as a reaction substrate and Catalyst F instead as a catalyst. The results of this experiment are shown in Table 1.

EXAMPLE 12 p-Xylene was oxidized by following the procedure of Example 11 while using Catalyst B instead as a catalyst. The results of this experiment are shown in Table 1.

EXAMPLE 13 p-Xylene was oxidized by following the procedure of Example 11 while using Catalyst C instead as a catalyst. The results of this experiment are shown in Table 1.

EXAMPLE 14

Toluene was oxidized. A reaction vessel containing 15 ml of acetic acid as a solvent was charged with 1.5 $\mu$mols of Catalyst A and 19 m.mols of toluene and cooled to 0° C. The reaction vessel, after having the gas phase part thereof filled to capacity with pure oxygen, was stoppered, then immersed in an oil bath kept at 120° C., and vigorously shaken for 24 hours to stir and incite to reaction the contained reactants. Then, the reaction solution was cooled to room temperature and the product was analyzed by liquid chromatography. It was consequently found that the yield of benzaldehyde was 0.5 mol % and the yield of benzoic acid was less than 0.1 mol % based on the amount of toluene charged. The results of this experiment are shown in Table 2.
Control 3
Toluene was oxidized by following the procedure of Example 14 while using 15 ml of dimethyl sulfoxide, 1.5 ml of 1,2-dichloroethane, and 0.1 ml of acetonitrile as solvents and Catalyst H as a catalyst. The results of this experiment are shown in Table 2.
Control 4
Toluene was oxidized by following the procedure of Example 14 while using Catalyst I instead as a catalyst. The results of this experiment are shown in Table 2.

EXAMPLE 15

Toluene was oxidized by following the procedure of Example 14 while using Catalyst B instead as a catalyst. The results of this experiment are shown in Table 2.

EXAMPLE 16

Toluene was oxidized by following the procedure of Example 14 while using Catalyst C instead as a catalyst. The results of this experiment are shown in Table 2.

EXAMPLE 17

Toluene was oxidized by following the procedure of Example 14 while using Catalyst E instead as a catalyst. The results of this experiment are shown in Table 2.

EXAMPLE 18

Toluene was oxidized by following the procedure of Example 14 while using Catalyst F instead as a catalyst. The results of this experiment are shown in Table 2.

EXAMPLE 19

Toluene was oxidized by following the procedure of Example 14 while using Catalyst F instead as a catalyst and 15 ml of acetic acid in the place of dimethyl sulfoxide as a solvent. The results of this experiment are shown in Table 2.

EXAMPLE 20

Toluene was oxidized by following the procedure of Example 14 while using 15 ml of dimethyl formamide instead as a solvent. The results of this experiment are shown in Table 2.

Control 5

Toluene was oxidized by following the procedure of Example 14 while using 1.5 μmols of tetrabutyl ammonium salt of one defective structure type [$\beta_2$-Si$_1$W$_{11}$O$_{39}$] and 4 μmols iron (III) acetylacetonate as catalysts. The results of this experiment are shown in Table 2.

EXAMPLE 21

Toluene was oxidized by following the procedure of Example 14 while using Catalyst J instead as a catalyst and 15 ml of water in the place of dimethyl sulfoxide as a solvent. The results of this experiment are shown in Table 2.

EXAMPLE 22

Toluene was oxidized by following the procedure of Example 14 while using 1.5 μmols of two defective type potassium salt K$_8$[γ-Si$_1$W$_{10}$O$_{36}$].12H$_2$O and 4 μmols of iron nitrate (III) nonahydrate as catalysts and 15 ml of water in the place of dimethyl sulfoxide as a solvent. The results of this experiment are shown in Table 3.

EXAMPLE 23

Toluene was oxidized by following the procedure of Example 18 while using Catalyst F instead as a catalyst and changing the reaction temperature to 200° C. The results of this experiment are shown in Table 3.

EXAMPLE 24

Toluene was oxidized by following the procedure of Example 18 while using Catalyst F instead as a catalyst and changing the reaction temperature to 230° C. The results of this experiment are shown in Table 3.

EXAMPLE 25 p-xylene was oxidized by following the procedure of Example 14 while using p-xylene in the place of toluene as a reaction substrate and Catalyst F instead as a catalyst. The results of this experiment are shown in Table 3.

EXAMPLE 26 p-Xylene was oxidized by following the procedure of Example 25 while using Catalyst G instead as a catalyst. The results of this experiment are shown in Table 3.

EXAMPLE 27 p-Cresol was oxidized by following the procedure of Example 14 while using p-cresol in the place of toluene as a reaction substrate and Catalyst F instead as a catalyst. The results of this experiment are shown in Table 3.

EXAMPLE 28 p-Acetoxy toluene was oxidized by following the procedure of Example 14 while using p-acetoxy toluene in the place of toluene as a reaction substrate and Catalyst F instead as a catalyst. The results of this experiment are shown in Table 3.

EXAMPLE 29

Ethyl benzene was oxidized by following the procedure of Example 14 while using ethyl benzene in the place of toluene as a reaction substrate and Catalyst G instead as a catalyst. The results of this experiment are shown in Table 3.

The entire disclosure of Japanese Patent Applications No. 2000-343673 filed on Nov. 10, 2000, No. 2000-343685 filed on Nov. 10, 2000, and No. 2000-343743 filed on Nov. 10, 2000, including specification, claims, drawings and summary are incorporated herein by reference in its entirety.

TABLE 1

| | | Example | | | | | | Control | |
|---|---|---|---|---|---|---|---|---|---|
| | | 1 | 2 | 3 | 4 | 5 | 6 | 1 | 2 |
| Catalyst | | Fe—POM | Fe—POM | Co—POM—K | Fe—POM—K | Co—POM | Ni—POM | 1-POM—Fe | 3-POM—Fe |
| Reaction substrate | | Toluene | Toluene | Toluene | Toluene | Toluene | Toluene | Toluene | Toluene |
| Yield (Basis:mol based on reaction substrate) | Benzaldehyde | 0.6 | 0.5 | 1.5 | 0.8 | 1.9 | 1.1 | 0.1 | 0.4 |
| | Benzoic acid | 2.7 | 2.6 | 4.0 | 3.2 | 4.7 | 3.4 | 0.2 | 1.3 |
| | p-Hydroxy benzaldehyde | | | | | | | | |
| | p-Hydroxy benzoic acid | | | | | | | | |
| | Acetophenone | | | | | | | | |
| | p-Acetoxy benzaldehyde | | | | | | | | |
| | p-Acetoxy benzoic acid | | | | | | | | |
| | p-Carboy benzaldehyde | | | | | | | | |
| | Telephthalic acid | | | | | | | | |

TABLE 1-continued

|  |  | Example | | | | | | |
|---|---|---|---|---|---|---|---|---|
|  |  | 7 | 8 | 9 | 10 | 11 | 12 | 13 |
| Catalyst |  | V—POM | V—POM | V—POM | V—POM | V—POM | Mn—POM | Au—POM |
| Reaction substrate |  | p-Cresol | Ethyl benzene | p-Acetoxy toluene | p-Toluylic acid | p-Xylene | p-Xylene | p-Xylene |
| Yield (Basis:mol based on reaction substrate) | Benzaldehyde |  |  |  |  |  |  |  |
|  | Benzoic acid |  |  |  |  |  |  |  |
|  | p-Hydroxy benzaldehyde | 2.8 |  |  |  |  |  |  |
|  | p-Hydroxy benzoic acid | 4.8 |  |  |  |  |  |  |
|  | Acetophenone |  | 4.2 |  |  |  |  |  |
|  | p-Acetoxy benzaldehyde |  |  | 3.5 |  |  |  |  |
|  | p-Acetoxy benzoic acid |  |  | 5.4 |  |  |  |  |
|  | p-Carboy benzaldehyde |  |  |  | 3.0 | 4.3 | 1.2 | 1 |
|  | Telephthalic acid |  |  |  | 7.0 | 12.0 | 3.7 | 4.9 |

TABLE 2

|  |  | Example | Control | | Example | | | | | | Control |
|---|---|---|---|---|---|---|---|---|---|---|---|
|  |  | 14 | 3 | 4 | 15 | 16 | 17 | 18 | 19 | 20 | 5 |
| Catalyst |  | Fe—POM | 1-POM—Fe | 3-POM—Fe | Mn—POM | Co—POM | Ni—POM | V—POM | V—POM | V—POM | 1 SiW—Fe |
| Reaction substrate |  | Toluene | Toluene | Toluene | Toluene | Toluene | Toluene | Toluene | Toluene | Toluene | Toluene |
| Solvent and amount thereof (ml) | Dimethyl sulfoxide |  | 5 | 5 | 5 | 5 | 5 | 5 |  |  | 5 |
|  | 1,2-Dichloroethane |  | 1.5 | 1.5 | 1.5 | 1.5 | 1.5 | 1.5 | 1.5 |  | 1.5 |
|  | Acetonitrile |  | 0.1 | 0.1 | 0.1 | 0.1 | 0.1 | 0.1 | 0.1 |  | 0.1 |
|  | Acetic acid | 15 |  |  |  |  |  |  |  | 15 |  |
|  | Water |  |  |  |  |  |  |  |  |  |  |
|  | Dimethyl formamide |  |  |  |  |  |  |  |  | 15 |  |
| Yield (Basis: mol based on reaction substrate) | Benzaldehyde | 0.5 | 0.2 | 0.4 | 0.8 | 0.8 | 0.7 | 1.2 | 1.4 | 1 | 0.1 |
|  | Benzoic acid | <0.1% | <0.1% | <0.1% | 0.1 | 0.1 | 0.1 | 0.1 | 0.3 | 0.1 | <0.1% |
|  | p-Hydroxy benzaldehyde |  |  |  |  |  |  |  |  |  |  |
|  | p-Hydroxy benzoic acid |  |  |  |  |  |  |  |  |  |  |
|  | 1-Phenylethyl alcohol |  |  |  |  |  |  |  |  |  |  |
|  | Acetophene |  |  |  |  |  |  |  |  |  |  |
|  | p-Acetoxy benzaldehyde |  |  |  |  |  |  |  |  |  |  |
|  | p-Acetoxy benzoic acid |  |  |  |  |  |  |  |  |  |  |
|  | p-Caraboxy benzaldehyde |  |  |  |  |  |  |  |  |  |  |
|  | Telephthalic acid |  |  |  |  |  |  |  |  |  |  |

TABLE 3

|  |  | Example | | | | | | | | |
|---|---|---|---|---|---|---|---|---|---|---|
| Control |  | 21 | 22 | 23 | 24 | 25 | 26 | 27 | 28 | 29 |
| Catalyst |  | K—POM—Mn | 2 SiW—Fe | V—POM | V—POM | V—POM | Au—POM | V—POM | V—POM | Au—POM |
| Reaction substrate |  | Toluene | Toluene | Toluene | Toluene | p-Xylene | p-Xylene | p-Cresol | p-Acetoxy toluene | Ethyl benzene |
| Solvent and amount thereof (ml) | Dimethyl sulfoxide |  |  | 5 | 5 | 5 | 5 | 5 | 5 | 5 |
|  | 1,2-dichloroethane | 1.5 | 1.5 | 1.5 | 1.5 | 1.5 | 1.5 | 1.5 | 1.5 | 1.5 |
|  | Acetonitrile | 0.1 | 0.1 | 0.1 | 0.1 | 0.1 | 0.1 | 0.1 | 0.1 | 0.1 |
|  | Acetic acid |  |  |  |  |  |  |  |  |  |
|  | Water | 15 | 15 |  |  |  |  |  |  |  |
|  | Dimethyl formamide |  |  |  |  |  |  |  |  |  |

TABLE 3-continued

| Control | | 21 | 22 | 23 | 24 | 25 | 26 | 27 | 28 | 29 |
|---|---|---|---|---|---|---|---|---|---|---|
| Yield (Basis: mol based on reaction substrate) | Benzaldehyde | 0.6 | 0.3 | 3.1 | 2.0 | | | | | |
| | Benzoic acid | <0.1% | <0.1% | 12.1 | 16.3 | | | | | |
| | p-Hydroxy benzaldehyde | | | | | | | 1.2 | | |
| | p-Hydroxy benzoic acid | | | | | | | 0.2 | | |
| | 1-Phenylethyl alcolol | | | | | | | | | 1 |
| | Acetophenone | | | | | | | | | 2.6 |
| | P-acetoxy benzaldehyde | | | | | | | | 1.8 | |
| | p-Acetoxy benzoic acid | | | | | | | | 0.5 | |
| | p-Carboxy benzaldehyde | | | | | 2.5 | 1.4 | | | |
| | Telephthalic acid | | | | | 1.8 | 0.5 | | | |

What is claimed is:

1. A method for the production of an aromatic carbonyl compound and/or an aromatic carboxylic acid by oxidation of an alkyl group of an aromatic compound possessing at least one alkyl substituent with a molecular oxygen-containing gas, which comprises effecting the oxidation by the use of a catalyst having at least one kind of element selected from the group consisting of phosphorus, silicon, and germanium as a hetero atom and at least one kind of element selected from the group consisting of molybdenum, tungsten, vanadium, and niobium as a poly atom and comprising a heteropolyoxometalate anion possessing two defective structure sites and at least one kind of element selected from the group of elements of Periods 4~6 of Groups IB, VA, VIIA, and VIII in the Periodic Table of the Elements, wherein the skeleton of the heteropolyoxometalate anion possessing the two defective structure sites is a Keggin type heteropoly acid ion possessing two defective structure sites including at least one of γ, δ, and ε isomers represented by the following general formula (1)

$$[Y_1M_{10}O_{36}]^{q-} \quad (1),$$

wherein Y is at least one kind of element selected from the group consisting of silicon, phosphorus, and germanium, M is at least one kind of element selected from the group consisting of molybdenum, tungsten, vanadium, and niobium, and q is a positive integer to be fixed by the valency of the elements Y and M.

2. A method according to claim 1, wherein two atoms of the at least one element selected from the group consisting of the elements of Periods 4~6 of Groups IB, VA, VIIA, and VIII in the Periodic Table of Elements are incorporated in the skeleton of the heteropolyoxometalate anion so as to form a shared edge.

3. A method according to claim 1, wherein the at least one kind of element selected from the group consisting of the elements of Periods 4~6 of Groups IB, VA, VIIA, and VIII is present in a ratio of not less than 0.001 atoms per molecule of the heteropolyoxometalate anion.

4. A method according to claim 1, wherein the at least one kind of element selected from the group consisting of the elements of Periods 4~6 of Groups IB, VA, VIIA, and VIII is at least partly incorporated in the skeleton of the heteropolyoxometalate anion.

5. A method according to claim 4, wherein the at least one kind of element selected from the group consisting of the elements of Periods 4~6 of Groups IB, VA, VIIA, and VIII is incorporated in a ratio of two atoms per molecule of the heteropolyoxometalate anion.

6. A method according to claim 4, wherein two elements selected from the group consisting of elements of Periods 4~6 of Groups IB, VA, VIIA, and VIII are incorporated in the skeleton of the heteropolyoxometalate anion in such a manner as to form a shared edge.

7. A method according to claim 1, wherein the reaction is carried out in at least one kind of solvent selected from the group consisting of organic solvents and water.

8. A method according to claim 1, wherein the reaction is carried out in an organic solvent.

9. A method according to claim 1, wherein the molar ratio of said catalyst to said reaction substrate is in the range of 1:1~1:1,000,000.

10. A method according to claim 1, wherein the weight ratio of solvent to said reaction substrate is in the range of 1:10~1000:1.

11. A method according to claim 1, wherein the amount of the molecular oxygen-containing gas to be used is not less than 0.01 mol per mol of the substrate.

12. A method according to claim 1, wherein the reaction is carried out at a temperature in the range of 0°~350° C. under a pressure in the range of normal pressure ~10 MPa.

* * * * *